United States Patent
Holland et al.

(10) Patent No.: US 8,106,229 B2
(45) Date of Patent: Jan. 31, 2012

(54) ORGANICALLY MODIFID SILICA AND USE THEREOF

(75) Inventors: Brian T. Holland, Oak Park, IL (US); Ji Cui, Naperville, IL (US); Timothy S. Keizer, Aurora, IL (US)

(73) Assignee: Nalco Company, Naperville, IL (US)

( * ) Notice: Subject to any disclaimer, the term of this patent is extended or adjusted under 35 U.S.C. 154(b) by 1178 days.

(21) Appl. No.: 11/443,515

(22) Filed: May 30, 2006

(65) Prior Publication Data

US 2007/0282122 A1   Dec. 6, 2007

(51) Int. Cl.
*C07F 7/10* (2006.01)

(52) U.S. Cl. .......... 556/423; 522/99; 522/170; 522/172

(58) Field of Classification Search .................. 556/423; 522/99.17, 172
See application file for complete search history.

(56) References Cited

U.S. PATENT DOCUMENTS

| | | | |
|---|---|---|---|
| 5,006,580 A | 4/1991 | Kasuya et al. | |
| 5,384,340 A | 1/1995 | Hara et al. | |
| 5,807,501 A * | 9/1998 | Burns et al. | 516/77 |
| 6,867,318 B1 | 3/2005 | Cui | |
| 6,887,518 B2 * | 5/2005 | Barthel et al. | 427/219 |
| 2002/0061407 A1 | 5/2002 | Colton et al. | |
| 2004/0039179 A1 | 2/2004 | McAuliffe et al. | |
| 2005/0234136 A1 | 10/2005 | Holland et al. | |
| 2006/0099429 A1 | 5/2006 | Domes et al. | |

OTHER PUBLICATIONS

Hah et al. {Simple preparation of monodisperse hollow silica particles without using templates, Chemical Communications (Cambridge, United Kingdom) (2003), (14), 1712-1713}.*

* cited by examiner

*Primary Examiner* — Elvis O Price
(74) *Attorney, Agent, or Firm* — Edward O. Yonter; Michael B. Martin

(57) ABSTRACT

Organosilane-modified nanoparticles of silica, having a particle size of no more than 1 micron, in which the organosilane resides throughout the entire volume of the nanoparticles and not just at the surfaces of the nanoparticle. The nanoparticles may be in a colloidal solution. They may be prepared by hydrolyzing an alkali silicate under acidic conditions to obtain a silicic acid dispersion, followed by adding an organosilane having hydroxyl and/or hydrolyzable groups to the dispersion under acid conditions; and then raising the pH of the dispersion to at least eight to form the nanoparticles. They may be used in an effective paint primer/protective coating formulation.

13 Claims, No Drawings

ORGANICALLY MODIFID SILICA AND USE THEREOF

BACKGROUND OF THE INVENTION

Organically modified silica particles are used as fillers for materials and the like, as well as a number of high technology uses. The silica may be in colloid form.

In the prior art, it is known to graft organically modified silanes onto a silica nanoparticle surface. Natural silica is covered with hydroxide groups, which are reactive with silanes having silanol or hydrolyzable groups, to bond the silane to the silica. Such silanes may carry a bonded organic radical such as an allyl group, an aminoalkyl group, or any of a variety of organic groups, which can change the surface characteristics of the silica.

By this invention, silica nanoparticles are provided in which an organosilane modifying agent is directly incorporated into the nanoparticles throughout their volume, rather than merely occupying the surface of the nanoparticles. Stronger modification of the characteristics of the silica nanoparticles can be achieved in this manner for improved fillers, for coatings and other formulations, abrasives, and other known uses of silica nanoparticles, which may be in a stable emulsion form.

Furthermore, such a product does not require a subsequent grafting step of reactive silane to its surface, so that the manufacturing process is simplified.

DESCRIPTION OF THE INVENTION

By this invention, as stated, organosilane-modified nanoparticles of silica are provided, having a particle size of no more than one micron, in which the organosilane typically is found throughout at least a substantial portion of the entire volume of the nanoparticle, and not just at the surfaces thereof. Accordingly, upon the breakage of a nanoparticle during use and handling, the newly formed, exposed surfaces can also carry the organosilane modifying agent. Furthermore, the physical characteristics of the modified silica thus formed will be different, providing opportunities for new types of fillers, abrasives having greater softness than pure silica, and other desirable characteristics. Such nanoparticles may find high technology uses in, for example, biotechnology, and also as foam stabilizers, catalysts, catalyst supports, abrasive and polishing agents, and the like.

In some embodiments, the particle size of the modified silica nanoparticles may be no more than 200 nanometers, for example about 3 to 150 nanometers in average particle diameter.

By this invention, formation of the nanoparticles of organosilane-modified silica may comprise the following steps: hydrolyzing an alkali silicate under acid conditions (less than pH seven) to obtain a silicic acid dispersion; adding an organosilane having hydroxyl and/or hydrolyzable groups to the dispersion (typically a solution); under acid conditions; (generally a pH of less than seven); and then raising the pH of the dispersion to at least about eight, to cause condensation of the organosilane and silicic acid, to form nanoparticles comprising an aggregate of silica and said organosilane.

In some embodiments, the silicic acid dispersion, prior to raising of the pH of the dispersion, comprises silicic acid molecules having an average of no more than about 10 silicon atoms per silicic acid molecule.

Typically, the pH of the dispersion may be raised to at least about 10 in the pH raising step of the above method.

Prior to the step of raising the pH as described above, the silicic acid and the organosilane may be mixed together in a dispersion, along with silica seeds comprising preformed particles (unlike the silicic acid dispersion) typically of a size range of 2 to 200 nm. In an embodiment, the silica seed particles comprise an average size of 2 to 200 nm and are added to the silicic acid-organosilane dispersion prior to raising the pH, to form enlarged nanoparticles. By the use of such silica seeds, larger nanoparticles, for example nanoparticles on the order of 60-70 nm can be easily synthesized, using preformed silica seeds having a size for example on the order of 10-30 nm. Without the use of such seeds, the synthesis of larger nanoparticles from silicic acid containing the organosilane is a longer and more difficult process. In the absence of such silica seeds, by the process of this invention, silica-organosilane nanoparticles on the order of 5-20 nm are easily made.

As a further advantage of the use of silica seeds up to about 200 nm in diameter, the resulting nanoparticles will have a pure silica interior, and then an outer volume having a discrete thickness below the particle surface of the thickness desired, which comprises the co-condensed silica and organosilane, so that the organosilane resides through an outer portion of the entire volume of the nanoparticles and not just at the surfaces of the nanoparticles, but the interior can be silane-free, for a saving of the more expensive silane material, while still achieving the advantages of having a discrete thickness of co-condensed silica-organosilane below the surface of the particles. Thus, typically, at least a substantial portion of the entire volume of the silica nanoparticles contains the organosilane, for example, at least about one tenth of the entire volume: optionally in the form of an outer coating surrounding the silica seeds.

Also, nanoparticles having less agglomeration can be synthesized, by making use of the added silica seeds as described above.

Alternatively, the silicic acid dispersion may be raised in its pH to at least eight prior to addition of the organosilane, having the effect of forming silica nanoparticles which do not contain the organosilane. Then, an additional aliquot of silicic acid solution, mixed with an organosilane having hydroxyl and/or hydrolyzable groups, may be added to the alkali dispersion of silica nanoparticles, causing further condensation on the surfaces of the silica nanoparticles of a mixture of silica and the organosilane. Thus, nanoparticles are formed which have silica centers that are free of organosilane, and outer portions that comprise a network of silica and organosilane, so that the organosilane is not just grafted to the surface of the particles, but is incorporated into the volume of the particle itself from the surface inwardly to a substantial degree. As previously stated, the entire volume of the nanoparticles which contain the organosilane may be, for example, at least about a tenth of the entire volume, which is a substantial portion, or a volume percentage ranging upwardly to the situation described above where the organosilane extends through 100% of the volume of the nanoparticles.

Optionally, the nanoparticle dispersion prepared in accordance with this invention may be deionized, to once again acidify the colloidal solution from an alkali pH such as pH 9 down to an acid pH on the order of 3-4, for stabilization in acidic formulations. This can be accomplished through cationic exchange in a conventional manner.

In some embodiments, the organosilane comprises a material of the formula $(R)_a Si(R^1)_b$, in which R is an organic radical having a reactive group comprising at least one of (1) nitrogen, (2) oxygen, (3) sulfur, (4) halide, and (5) at least one unsaturated carbon-carbon linkage; $R^1$ is a hydrolyzable group or an alkyl group, at least two of said $R^1$ groups being hydrolyzable groups; a is 1 or 2; and b is 2 or 3, the total of a and being.

R has a reactive group which comprises at least one of (1) nitrogen, (2) oxygen, (3) sulfur, and (4) at least one unsaturated carbon-carbon linkage. Examples of such materials may be allyl, 3-glycidoxypropyl; 3-aminopropyl; dimethylaminopropyl; 3-iodopropyl; 3-chloropropyl; acetoxypropyl; 3-methacryloxypropyl; and mercaptopropyl. It can be seen that these R groups are organic radicals having a reactive group so that the silane, in which $R^1$ comprises at least two of hydroxyl or hydrolyzable groups, can be bonded in a condensation reaction with the silicic acid, so that the silane groups connect with silicate groups by the usual siloxane linkages, carrying the R groups of organic radicals having a reactive group into the matrix of the condensing molecules that form the nanoparticles, imparting to the nanoparticles desired, different characteristics, and the capability to bond through the reactive groups of the organic R radicals to other materials.

$R^1$, as stated, can be hydroxyl, although, as is known, the hydroxyl groups tend spontaneously to condense if more than one of them are bonded to the same silicon atom. $R^1$ therefore preferably comprises hydrolyzable groups, although an alkyl group may be present as one of the $R^1$ groups if desired. The hydrolyzable groups may comprise lower alkoxy, for example, methoxy, ethoxy or propoxy, up to typically about six carbon atoms. Another hydrolyzable group is acetoxy, and other, known groups. These hydrolyzable groups react in the presence of the hydroxyl groups and moisture in the silica, to permit condensation and bonding of the silane to the silica in a known manner.

As stated, a is 1 or 2, meaning that there are one or two organic radicals having reactive groups in the silane molecule, while b is at least two, for good results.

Examples of the organosilane materials which can be used are alkoxy silanes such as allyltrimethoxysilane, 3-glycidoxytrimethoxysilane, 3-aminopropyltrimethoxysilane, 3-iodopropyltrimethoxysilane; 3-chloropropyltriethoxysilane; acetoxytriethoxysilane; and 3-thiopropyltrimethoxysilane.

Alternatively, the organosilane may comprise a material of the formula

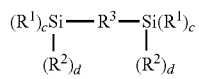

in which $R^1$ is a hydrolyzable group; $R^2$ is a hydrocarbon radical; $R^3$ is a divalent organic radical, c is 2 or 3; d is 0 or 1, the c and d relating to each silicon atom totaling 3.

Referring to the above formula, $R^1$ may be hydroxyl or a hydrolyzable group as previously discussed. $R^2$ may be a hydrocarbon radical if present, such as methyl, ethyl, or phenyl.

$R^3$ is a divalent organic radical, for example dimethylene, 2-ethyl hexamethylene, phenylene or similar radicals, optionally modified to have a reactive group as previously described comprising at least one of (1) nitrogen, (2) oxygen, (3) sulfur, and (4) at least one unsaturated carbon-carbon linkage. Thus, an unsaturated divalent hydrocarbon radical may be used as $R^3$ if desired such as phenylene, or an unsaturated olefin divalent radical, as a candidate for $R^3$. If $R^3$ has a reactive group, as described above, it may participate in further reactions to bond the modified silica to a compatible substrate in a coating or the like. If $R^3$ is nonreactive, it still is present to modify the silica, to provide modified abrasives and the like. An example of such material is 1, 2 bistrimethoxysilylethane.

The alkali silicate which is used to obtain the silicic acid dispersion may be hydrolyzed by a cationic exchange material which, in conventional manner, sequesters the alkali groups of an alkali silicate. Such alkali groups may comprise alkali metals such as sodium, potassium, and other alkali metals; ammonium; alkaline earth metals such as calcium and magnesium; and the like. Thus, sodium, potassium, or ammonium silicate, for example, may be passed through a cationic exchange resin of known type to form the silicic acid dispersion, which will, upon removal of the alkali ions, exhibit "acid conditions" (a pH of less than seven).

Thereafter, the organosilane having the silanol or hydrolyzable groups may be added to the silicic acid dispersion while the pH is still on the acid side, i.e. less then 7. Under these acid conditions, silicic acid tends to stay in relatively uncondensed form, for example, the molecules having an average of no more than 10 silicon atoms. Then, the pH may be raised to at least 8 and typically 10, causing condensation of the dispersion to form the desired nanoparticles which, by control of reaction conditions in known manner, can be of the desired size of less than 1 micron, and typically about 10-100 nm. Particularly, temperature and rate of combining of the ingredients can provide such control.

The nanoparticles formed may be used in known uses for silica nanoparticles, but with the nanoparticles providing significant differences in performance because of their different physical properties, due to the presence particularly of the organic components. The nanoparticles may be stored as colloidal solutions.

Further in accordance with this invention, the nanoparticles produced herewith may be incorporated into a protective coating for metal surfaces, which coating may serve as an anticorrosion coating, but it also may serve as a priming coating for paint.

The protective coating may include a formulation of generally conventional ingredients for coating formulations, but also comprising (a) one part by weight of the organosilane-modified silica nanoparticles as described above, and (b) from 0.3 to 3 parts by weight of the reaction product of (1) a compound comprising a polyamine in which a plurality of amine groups are bonded to at least one radical selected from the group consisting of hydrocarbon and hydrocarbon ether groups that separate nitrogen atoms of said amine groups by at least four intermediate atoms in a chain, and (2) a silane which carries a plurality of silicon-bonded hydrolyzable groups, plus a silicon-bonded organic group that is covalently reactive with, and which bonds with, said amine group, to provide a reaction product molecule which comprises an average of at least 2.5 and typically no more than about four of said hydrolyzable silane units per molecule.

Examples of this reaction product of ingredient (b) above are illustrated in Cui U.S. Pat. No. 6,867,318 B1, the material being taught as a composition for coating of aluminum. The material exhibits good surface coating and adhesion to metal, being comparable in performance with the conventional, chromated aluminum surfaces, the best of which are being removed from the market because of the carcinogenic characteristic of $Cr^{+6}$.

However, coatings of the materials as described in U.S. Pat. No. 6,867,318 are relatively smooth in some circumstances. It is desirable to have chromium free coatings that are rougher in their surface on a nanoscale basis. By this invention, with the addition of the organosilane-modified silica to the above-described coating formulation, a microroughening of the surface and a significant improvement in paint adhesion has been achieved, for example, using the organosilane-modified silica as described above having a particle size of about 5-20 nm.

The phrase "silicon-bonded organic group that is covalently reactive with and which bonds with said amine group" is defined as an organic group which has a moiety or portion, such as an epoxy ring, that is spaced from the silicon atom, and is covalently reactive with an amine group, to bond the silicon bonded organic group, and the silicon atom that it carries, with the molecule that carries the amine group. An example of such a silicon-bonded organic group is 3-glycidoxypropyltrimethoxysilane. Thus, in a compound used in this invention, the silicon atom per se does not react with the amine group, but is spaced from the amine group by the silicon bonded organic group.

In some embodiments for ingredient (b), essentially two amine groups of a polyamine compound are present per molecule of reaction product, each amine group comprising a primary amine prior to reaction with the silane. Thus, the original reactant to form the reaction product may be a diamine with two primary amine groups separated by the hydrocarbon or hydrocarbon ether groups that separate the nitrogen atoms of the amine groups.

In some embodiments, the polyamine may comprise about one molar part of C,C,C-trimethyl-1,6-hexane diamine (such a carbon structure is shown in U.S. Pat. No. 6,867,318), reacted with a silane that has bonded hydrolyzable groups and a silicon-bonded organic epoxide radical, such as 3-glycidoxypropyltrimethoxysilane.

In some embodiments, the polyamine has a molecular weight in the range of 100 to 10,000. Good results can be achieved when one molar part of the diamine is reacted with at least 2.5 molar parts of the silane, to provide a composition with molecules containing both silicon and amine groups and typically at least 2.5 hydrolyzable silane groups per molecule, up to typically about six silane groups per molecule, on average.

The known alkylene ether polyamines (available from Huntsman International, LLC located in The Woodlands, Tex., and sold under the tradename Jeffamine®) may be used in the preparation of the reaction product of ingredient (b).

The polyamine may also have amine groups bonded to a branched alkylene radical of at least 6 carbon atoms, or an arylene radical that separate the amine nitrogen atoms by at least four intermediate atoms in the chain, one example of that being the TG13 and TG14 materials disclosed in the above cited patent. Unbranched alkylene radicals such as hexamethylene may also be used to form the polyamine used in forming ingredient (b). Tetramethylene diamine may also be used, as well as other polyamines having a central alkylene radical with 4 to 22 carbon atoms.

Aromatic polyamine materials may be used, where $R_1$ through $R_8$ of these aromatic formulations may comprise hydrogen or lower alkyl groups up to about 6 carbon atoms. These polyamines may be respectively reacted with the hydrolyzable silanes described herein to provide the polyfunctional, cross-linkable materials used in this invention. Examples are shown below:

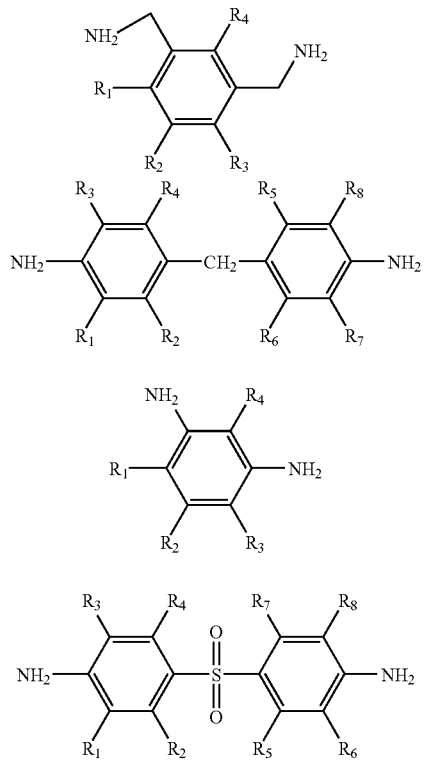

As another category of polyamines which may be used in this invention, providing a hydrocarbon ether or polyether group with at least two attached amine groups, is shown below. Jeffamine-type materials may also be used.

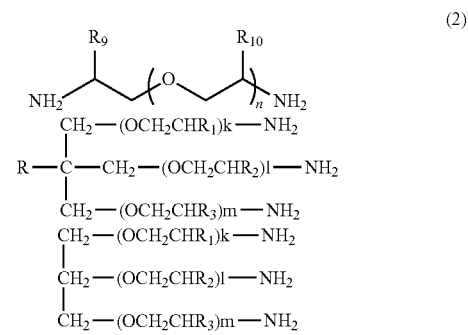

As used in the formulas immediately above, n, k, l and m are independently integers from 1 to 3,000. In the formulae above, $R_1$ through $R_{10}$ may independently be hydrogen or organic groups of up to 4 carbon atoms. Typically, each of the numbered R groups in the groups of formulas (1) and (2) immediately above may be hydrogen.

Other examples of aromatic diamines and polyamines, for reaction with the polysilanes described herein (thus forming an R group that links amine groups) are as follows:

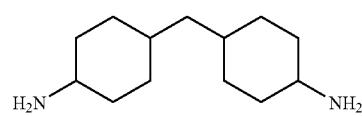

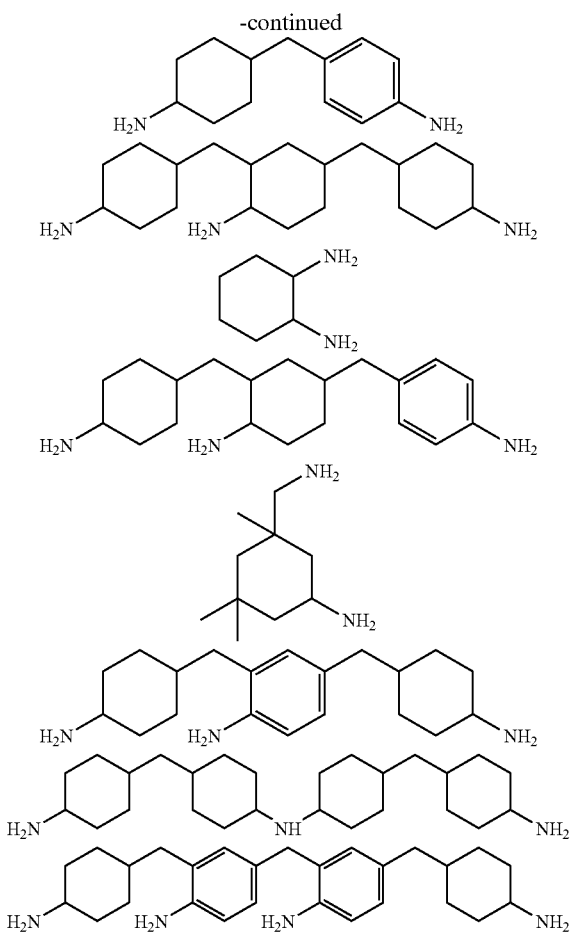

In the reaction of a polyamine with the silane carrying silicon-bonded hydrolyzable groups as described above, the multifunctional amine "backbone", represented by R above covalently links through the amine groups to the silane "arms" (the R' groups) as above, to form amine silane adducts. In the embodiments where an epoxy silane is used, the adducts are formed by the creation of amine-epoxy linkages, with a varying number of the amine-epoxy linkages depending on the molar ratio, to provide differing effects as described above. The resulting silane-modified amine adducts thus carry multiple terminal silyl groups that are bonded to hydrolyzable groups such as alkoxy. These are capable of high-degree, intermolecular cross-linking by hydrolysis and linking of the hydrolyzable groups as the material is cast from a solution or dispersion and cured into a crosslinked, corrosion protecting film. Excellent results have been achieved.

The polyamine-epoxy silane adducts of ingredient (b) may be water-soluble or water dispersible especially when neutralized with an organic acid such as acetic acid. Therefore the technology can be compliant with low VOC emission regulations. Also, the coating solution is free of hazardous metals such as chromium. Furthermore, an aqueous 5% solution of a preferred polyamine silane adducts exhibits a long tank life of greater than three weeks without degradation of anticorrosion performance, indicating the hydrodynamic stability of particularly the amine-epoxy silane adducts in water. Thus, the process of use of the materials of this invention can be fully compatible with the existing equipment of customers.

The coating can be applied to metal substrates such as aluminum and alloys thereof from water solution, either by spraying, dipping, or the like. The entire process may be accomplished by an initial step of alkaline cleaning, a double rinse, dip coating, and curing by annealing with drying. Typical annealing temperatures range from room temperature of about 20° C. to an elevated temperature of about 120° C., with higher temperatures accelerating the cross-linking process of the coating.

The reaction conditions for making polyamine-epoxy silane adducts of ingredient (b) are generally quite mild. For the epoxy silanes the conditions of making adducts may often be simply a period of reaction of 24 to 48 hours at about 22° C., or a period of about 3 hours at 70° C., the reaction being typically performed in alcohol solvent. The reaction yield is high, usually exceeding 90% of the amine present.

Resulting coatings containing ingredient (b) can be thin and clear, being typically on the order, after drying, of 0.3 to 1 micron in thickness (in the case where it is dip-coated from 5 weight percent water solution). The material of this invention can be invisible to the eyes, and therefore does not interfere with the metal's natural luster, contrary to the chromium based conversion coatings.

Examples of epoxy silanes which may be used in this invention to make ingredients (a) and/or (b) comprise 3-glycidoxypropyltrimethoxysilane: 3-glycidoxypropylmethyldimethoxysilane; 3-glycidoxypropyltriethoxysilane; and 3-glycidoxypropylmethyldiethoxysilane.

A preferred solvent for conducting the adduct-forming reaction to make ingredient (b) is an alcohol or alcohol-containing solvent in which the alcohol content is 30% by volume or more, typically about 50 volume percent. The preferred alcohols are the alkyl alcohols, linear or branched, of no more than 6 carbon atoms, specifically methanol or ethanol, particularly when using a water-based working solution.

The preferred synthesis temperature may typically range from about 70° F. to 250° F. Higher temperatures generally give faster reaction kinetics. In a typical reaction that uses methanol as a solvent without pressure, the reaction temperature may be held constant at the boiling point of methanol, 150° F., for up to about 6 hours. Using a reaction vessel that can sustain pressure can bring the reaction temperatures higher than the point of boiling alcohol, thus achieving faster reaction rate at 200° F. and 5 atmosphere pressures.

The reaction in methanol between the epoxy silane and the polyamine can go to completion with greater than 90% yield in 3 hours.

The prepared reactant loading in the total solvent-reactant mixture is generally not critical, and thus may range from about 1-95%. More preferred reactants are on the order of 70% of the total weight of the mixture, or less.

The resulting multifunctional amino silane produced can be applied, with or without further dilution with organic solvent, as a solvent-borne coating onto metallic substrates. Typically, the multifunctional silane will be at least partially hydrolyzed into silanol form. This partial hydrolysis can be achieved by adding a small amount of water to the multifunctional silane-alcohol solvent mixture, or the water may be present in the reaction mixture initially. For a silane-solvent 50:50 mixture by weight, it is preferred that about 2 to 5 parts by weight of water should be present for every 100 parts by weight of the polyamine-silane adduct.

As a preferred method for dissolving the multifunctional polyamine-silanes in water, which may be required in certain situations where high volatile, organic solvent emissions are undesirable, the multifunctional polyamine-silane may be converted into the ammonium or salt form with acids. The preferred acids are volatile organic acids with a boiling point less than 350° F. including but not limited to acetic acid and formic acid.

Thus, by this invention, conversion coatings for aluminum are provided which are free of chromium, and which also exhibit excellent characteristics as paint primers. The coatings are useful on aluminum, but also on aluminum alloys and other materials, such as steel, zinc, copper, chromium, zirconium, manganese, cobalt, nickel, titanium, molybdenum, for example, and alloys thereof.

The coating formulations may be conventionally formulated into colloidal solutions for application which are either water based or organic solvent based, and may be applied by spraying or dipping. Typically, the process of application thereof to metals comprises (1) alkaline cleaning, (2) a double rinse, (3) dip coating in the coating formulation of this invention, having appropriate solvents and other conventional ingredients, and (4) thermal curing.

The coating of this invention may be thin and clear, being about a tenth micron in thickness when dip-coated on metal like aluminum from a 1 wt. % total solids water (colloidal) solution. The coating is typically invisible to the eyes, and therefore is not colored, as are chrome coatings. Chrome coatings interfere with the metal's natural luster.

Surface active agents may be optionally added to improve the wetting of the materials of this invention on a metal surface. Anionic, cationic, and nonionic surfactants can be added to the film forming material in a concentration of typically 0.05-2 weight percent of the total solution weight. Anionic or nonionic surfactants are typically preferred. Defoamers may also be added, typically at a weight percent of about 0.1-3 percent, based on the total solution weight.

Corrosion inhibitors may also be added, including both cathodic and anodic inhibitors, optionally in the amount of 0.1-5 weight percent of the solids present.

The above disclosure and the examples below are offered for illustrative purposes only, and are not intended to limit the scope of the invention of this application, which is as defined in the claims below.

EXAMPLE 1

A silicic acid solution was produced by passing a solution of 25 grams of sodium silicate in 57.37 g of deionized water through a column containing Dowex 65OC(H$^+$) cation exchange resin. About 40 ml. of resin for each 100 grams of sodium silicate solution plus water was used. The resulting product comprises a silicic acid solution at a pH of about 3.5.

To this freshly made solution was added 5 grams of 3-glycidoxypropyltrimethoxysilane, the pH of the mixture being maintained at less than 7 throughout the mixing.

This mixture of silicic acid and organosilane in water was then dripped into a reaction flask at a rate of 10 ml per minute, with the reaction flask containing 31 ml of water with sufficient sodium hydroxide to provide a pH of about 9, the water solution being heated and under agitation. Specifically, 64 weight percent of the silicic acid; 5 weight percent of the organosilane; about 30.7 weight percent of deionized water and 0.3 wt. percent of sodium hydroxide was combined in the flask. The mol. ratio of $SiO_2$/3-glycidoxypropyltrimethoxysilane was 4.3/1.

The resulting solution is a clear, colloidal solution comprising colloidal particles of about 10-20 nanometers (nm) diameter, the particles comprising a bonded network of $SiO_2$ units and organosilane units.

EXAMPLE 2

In this Example, 0.25 gm. of 3-aminopropyltrimethoxysilane was added to 5.0 gm. of water containing 0.15 gm. of acetic acid. The solution was kept in an ice bath to keep the silane stable. Separately, 25.6 gm. of a silicic acid solution like that of Example 1 was prepared, containing 0.085 wt. percent $SiO_2$. The silane solution was added to the silicic acid solution, and mixed thoroughly. This solution was then added at a rate of 1.5 ml/min to a reaction flask containing 0.4 gm. of 50 wt. percent sodium hydroxide solution, mixed with 68.6 gm. of water, heated to 80° C.

The resulting colloidal solution was clear, comprising nanoparticles of a network of $SiO_2$ units and aminoalkylsilane units, covalently bonded together in siloxane linkages, and having a particle size of about 5.5 nm., as determined by quasi-elastic light scattering (QELS).

EXAMPLE 3

An experiment similar to the above was repeated, by placing 0.25 gram of thiopropyltrimethoxysilane into 5.0 gm. of water containing 0.15 gm of acetic acid. The solution was kept in an ice bath, to keep the silane stable.

Separately, 25.6 gm. of silicic acid solution was generated, in a manner similar to Example 1, with the solution containing 0.085 wt. percent $SiO_2$. The silane solution was added to the silicic acid solution, and mixed thoroughly, the pH being acidic.

The resulting mixture was then added a rate of 1.5 ml per minute to a reaction flask containing 0.4 gm. of 50 wt. percent sodium hydroxide solution, mixed with 68.6 gm. of water, at a temperature of 80° C. The expected alkali condensation of the silane and silicic acid took place, resulting in composite particles of silica and silane having a particle size of about 5.5 nm., as determined by QELS.

EXAMPLE 4

In this example, the direct synthesis of vinyl-doped colloidal silica nanoparticles is disclosed, where the vinyl groups are located only on an outside portion of the colloid, but the nanoparticles are made in situ, without the addition of preformed silica nanoparticles (as is disclosed in the next example).

A batch of silicic acid solution was prepared in the manner of Example 1, the amount being 56.2 gm. of solution. Of this amount, 46.2 gm. of the silicic acid solution was added to a reaction mixture containing 0.4 gm. of 50 wt. percent sodium hydroxide solution in 40.0 gm. of water, at a temperature of 90° C. The silicic acid solution was added to the hot solution at a rate increasing from 0.22 ml to 0.8 ml per minute over a period of two hours, resulting in the condensation of the silicic acid into nanoparticles that remained in a silica colloidal solution.

After completion of this reaction, another 10 gm. of the above, original silicic acid solution, to which was added 0.5 gm. of vinyltrimethoxysilane, 0.5 gm. of acetic acid, and 33.3 gm. of water, was added at a rate of 12 ml per minute to the above silica colloidal solution.

The resulting colloidal solution comprised generally spherical particles having a particle diameter of about 25 nm. as obtained by transmission electron micrograph. The inner portion of the particles comprised substantially pure silica, while an outer portion of the particles comprised condensed silica and organosilane.

EXAMPLE 5

In this example, colloidal seed particles serve as a base on which silicic acid and an organosilane are co-condensed. Sixteen grams of colloidal silica seed particles having a size of about 20 nm. were added to 250 gm. of water containing 2.2 gm. of 50% sodium hydroxide solution to provide a pH in excess of 8, and to form a "heel" solution for the reaction. Optionally, added water may be added.

Separately, 15 gm. of 3-glycidoxypropyltrimethoxysilane was added to freshly made silicic acid solution of the type prepared in Example 1, at a temperature of 5° C. and a pH of about 3.5.

The reaction "heel" solution was heated to 80° C. with agitation, while the silicic acid-organosilane solution was slowly added over a period of about four hours.

The resulting product, comprising a solution of silica nanoparticles having an outer coating of organic modified silica, was passed through a column of regenerated cationic exchange resin (Dowex 650C). The resulting organic modified silica solution was collected, and formed a stable solution at a pH of less than 3.7.

EXAMPLE 6

The organosilane-modified colloidal silicas made as specified in Examples 1 and/or 2 above were mixed with the trisilane material identified as TG13 (and TG13R) in U.S. Pat. No. 6,867,318 B1, the disclosures of which are incorporated by reference in this application. The proportions of such mixing are as specified in Table 1 below for each experimental run. The mixture of the organosilane modified silica colloidal solution and TG13 was made in an aqueous solution, with a total concentration of 1 weight percent solids and a pH of 5, adjusted with acetic acid.

Aluminum panels were cleaned with Nalco Globrite 45 IL alkaline cleaner, and rinsed thoroughly with deionized water. The aluminum alloy was the copper-containing alloy AL2024.

The cleaned, aluminum panels were dip-coated into the 1% total solids solution described above in each of the specific experiments illustrated in Table 1, and dried at an oven at 250° F. for 15 minutes.

Sherwin Williams polyester white paint was then applied over the coated aluminum panels via a roller bar, to achieve a thickness of 20-30 microns of the paint layer, and the paint was cured at 350° F. for 20 minutes.

The panels were scribed with scratches three inches long, using a sharp point to expose bare metal in the scribe line. The respective aluminum panels of the various experiments were then subjected to a 1,000 hour salt spray, and the amount of blistering and opening of the paint along the scribe line was recorded.

Experiments A-C below in Table 1 utilized the silica-epoxy silane (epoxysilica) nanoparticles prepared in Example 1. Experiments D-F utilized the silica-aminosilane (aminosilica) nanoparticles of Example 2. Experiments G, H, and I utilized a one-to-one mixture (by weight) of the epoxy silane and aminosilane nanoparticles. The ratio of TG13 to the modified silica nanoparticles (by weight) is expressed in each case in Table 1, as are the results, expressed as a distance in millimeters of transverse opening of the scribe line after the 1,000 hour salt spray treatment.

Experiment J is a run where the painted aluminum panel was treated merely with a 1% solution of TG13, without the nanoparticles, and heat cured as specified in this Example.

Experiment K related to the painted panel without any paint priming, so that the paint was laid upon the bare alloy.

The results show that experiments A-I, utilizing pretreatment of aluminum with the combination of TG13 and organosilane-modified silica nanoparticles, provide improved paint adhesion results, compared with the pretreatment of pure TG13, and greatly improved results over the panel where the paint was directly applied to the aluminum alloy without an intervening pretreatment layer.

TABLE 1

| Experiment | Composition | TG13/Silica Ratio (by. wt.) | 1000 Hr. Salt Spray-blister width (mm) |
|---|---|---|---|
| A | TG13 + epoxysilica | 1 to 1 | 1 |
| B | TG13 + epoxysilica | 2 to 1 | 0.5 |
| C | TG13 + epoxysilica | 1 to 2 | 1.5 |
| D | TG13 + aminosilica | 1 to 1 | 0.5 |
| E | TG13 + aminosilica | 2 to 1 | 0.5 |
| F | TG13 + aminosilica | 1 to 2 | 0 |
| G | TG13 + epoxy-aminosilica 1 to 1 mix | 1 to 1 | 0.5 |
| H | TG13 + epoxy-aminosilica 1 to 1 mix | 2 to 1 | 0 |
| I | TG13 + epoxy-aminosilica 1 to 1 mix | 1 to 2 | 0.5 |
| J | pure TG13 1% | | 2 |
| K | Blank | | 5 |

EXAMPLE 7

An aqueous coating composition containing 5 Wt. percent of TG 14 (U.S. Pat. No. 6,867,318) and 0.5 wt. percent epoxysilane-modified silica of Example 1 produced a film with a Hardness of over 8H by a pencil hardness test, in contrast with a pure TG 14 film (U.S. Pat. No. 6,867,318 B1) produced in a comparable manner, which had a pencil hardness test result of 4H. Both films were baked at 250 degrees F. for 15 minutes. The increased hardness implies abrasion resistance imparted by the modified silica.

What is claimed is:

1. A method of preparing nanoparticles of organosilane-modified silica, the method comprising:
   (a) hydrolyzing an alkali silicate under acid conditions to obtain a silicic acid dispersion;
   (b) adding an organosilane having hydroxyl and/or hydrolyzable groups to the dispersion under acid conditions to form a silicic acid-organosilane dispersion, wherein silica seed particles of an average size of 2 to 200 nm are added to the silicic acid-organosilane dispersion; and
   (c) raising the pH of the dispersion to at least eight to cause condensation of the organosilane and silicic acid to form nanoparticles comprising an aggregate of silica and said organosilane.

2. The method of claim 1 in which said silicic acid dispersion comprises silicic acid molecules having an average of no more than about ten silicon atoms per silicic acid molecule, prior to raising the pH.

3. The method of claim 1 in which said organosilane comprises a material of the formula $(R)_a Si(R^1)_b$, in which R is an organic radical having a reactive group comprising at least one of (1) nitrogen, (2) oxygen, (3) sulfur, and (4) at least one unsaturated carbon-carbon linkage; $R^1$ is a hydrolyzable group or an alkyl group, at least two of said $R^1$ groups being hydrolyzable groups; a is 1 or 2; and b is 2 or 3, the total of a and b being 4.

4. The method of claim 1 in which said organosilane comprises a material of the formula

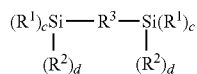

in which $R^1$ is a hydrolyzable group; $R^2$ is a hydrocarbon radical; $R^3$ is a divalent organic radical, c is 2 or 3; d is 0 or 1, the c and d relating to each silicon atom totaling 3.

5. The method of claim 4 in which $R^3$ has a reactive group comprising at least one of: (1) nitrogen, (2) oxygen, (3) sulfur, and (4) at least one unsaturated carbon-carbon linkage.

6. The method of claim 1 in which the nanoparticles formed have an average size of no more than one micron.

7. The dispersion of nanoparticles made by the process of claim 1.

8. The method of claim 1 in which the organosilane comprises an allyltrialkoxysilane.

9. The method of claim 1 in which the organosilane comprises a glycidoxytrialkoxysilane.

10. The method of claim 1 in which the organosilane comprises an aminoalkyltrialkoxysilane.

11. The method of claim 1 in which said alkali silicate is hydrolyzed by cationic exchange resulting in silicic acid at an acid pH.

12. The method of claim 1 in which the nanoparticles formed have an average size of 5-150 nm.

13. The method of claim 1 in which the pH of the dispersion is raised to at least ten.

* * * * *